United States Patent [19]
Benson et al.

[11] Patent Number: 5,483,973
[45] Date of Patent: Jan. 16, 1996

[54] NEEDLE STOPPER AND NEEDLE REMOVAL DEVICE

[75] Inventors: Carl L. Benson, Wyckoff; Anthony J. Kosinski, Murray Hill, both of N.J.

[73] Assignee: Becton, Dickinson and Company, Franklin Lakes, N.J.

[21] Appl. No.: 125,575

[22] Filed: Sep. 23, 1993

Related U.S. Application Data

[63] Continuation-in-part of Ser. No. 969,496, Oct. 30, 1992, abandoned.

[51] Int. Cl.$^6$ .............................. A61B 5/00; B65D 81/00
[52] U.S. Cl. ........................... 128/760; 128/763; 604/192
[58] Field of Search ..................................... 128/893, 760, 128/763, 765, 766, 919; 604/192, 263, 187, 110; 206/363, 364, 365, 367, 368

[56] References Cited

U.S. PATENT DOCUMENTS

| | | | |
|---|---|---|---|
| 3,637,072 | 1/1972 | Narusawa et al. | |
| 4,178,941 | 12/1979 | Raitto | 128/763 |
| 4,213,456 | 7/1980 | Bottger. | |
| 4,286,591 | 9/1981 | Raines. | |
| 4,340,067 | 7/1982 | Rattenborg | 128/763 |
| 4,444,310 | 4/1984 | Odell | 206/366 |
| 4,735,617 | 4/1988 | Nelson et al. | 604/192 |
| 4,774,963 | 10/1988 | Ichikawa et al. | 128/763 |
| 4,795,443 | 1/1989 | Permenter et al. | 604/198 |
| 4,886,071 | 12/1989 | Mehl et al. | 128/760 |
| 5,078,695 | 1/1992 | Farrar, Jr. et al. | 604/192 |
| 5,078,696 | 1/1992 | Nedbaluk | 604/192 |
| 5,084,027 | 1/1992 | Bernard | 604/192 |
| 5,303,713 | 4/1994 | Kurose | 128/763 |
| 5,304,148 | 4/1994 | Lannoye et al. | 604/192 |
| 5,360,011 | 11/1994 | McCallister | 128/763 |

FOREIGN PATENT DOCUMENTS 2209470  5/1989  United Kingdom ................... 607/263

Primary Examiner—C. Fred Rosenbaum
Assistant Examiner—V. Alexander
Attorney, Agent, or Firm—John L. Voellmicke

[57] ABSTRACT

A needle stopper for use with a hypodermic syringe such as an arterial blood gas syringe includes a shell having a bottom, an open top and a needle-receiving chamber therebetween. The bottom is configured to support the needle stopper in an upright orientation. The needle-receiving chamber is dimensioned to receive needle cannula and to engage a needle hub connected to the cannula. The chamber is at least partly filled with a sealing material that can occlude the tip of a needle cannula. The upright orientation of the needle stopper enables one-handed insertion of the needle cannula into the needle-receiving chamber for occluding the needle tip. Engagement of the needle stopper with the needle hub enables safe and convenient separation of the needle hub and cannula from the syringe barrel for disposal. The tip of the syringe barrel then may be capped and sent to a laboratory for analysis of fluids therein.

3 Claims, 6 Drawing Sheets

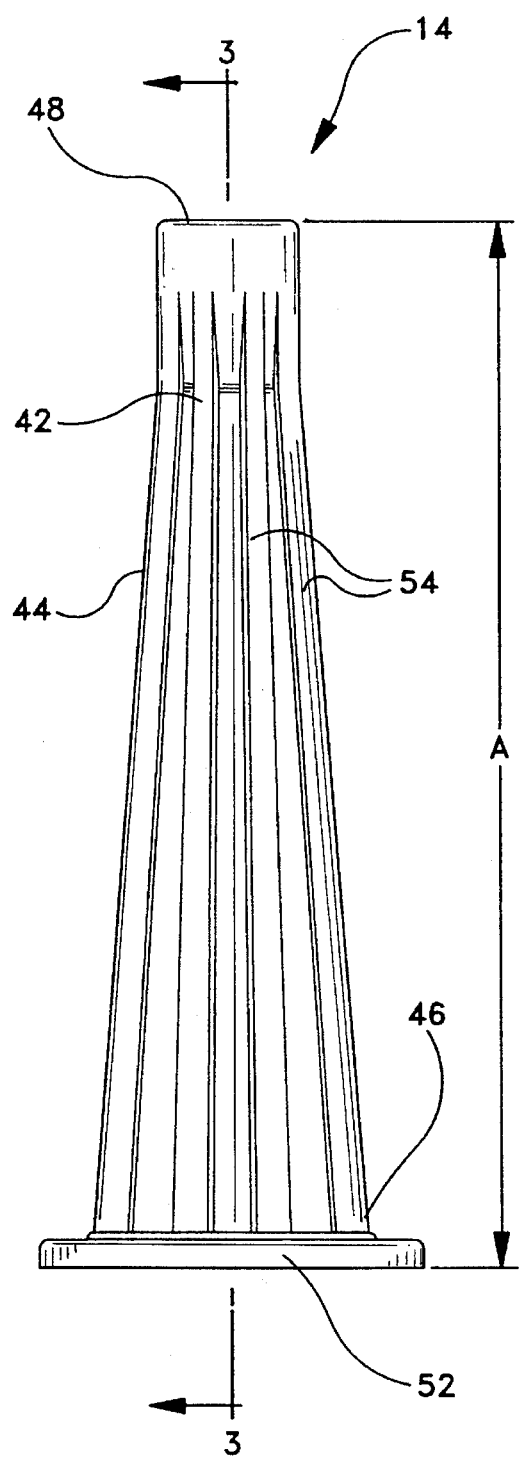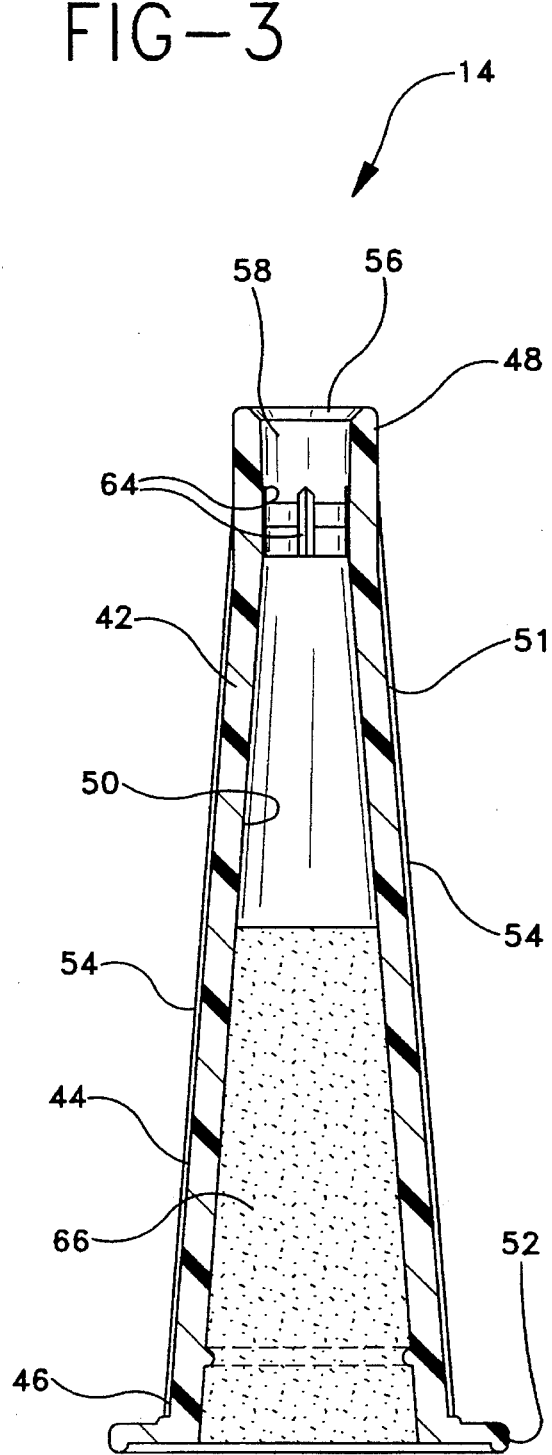

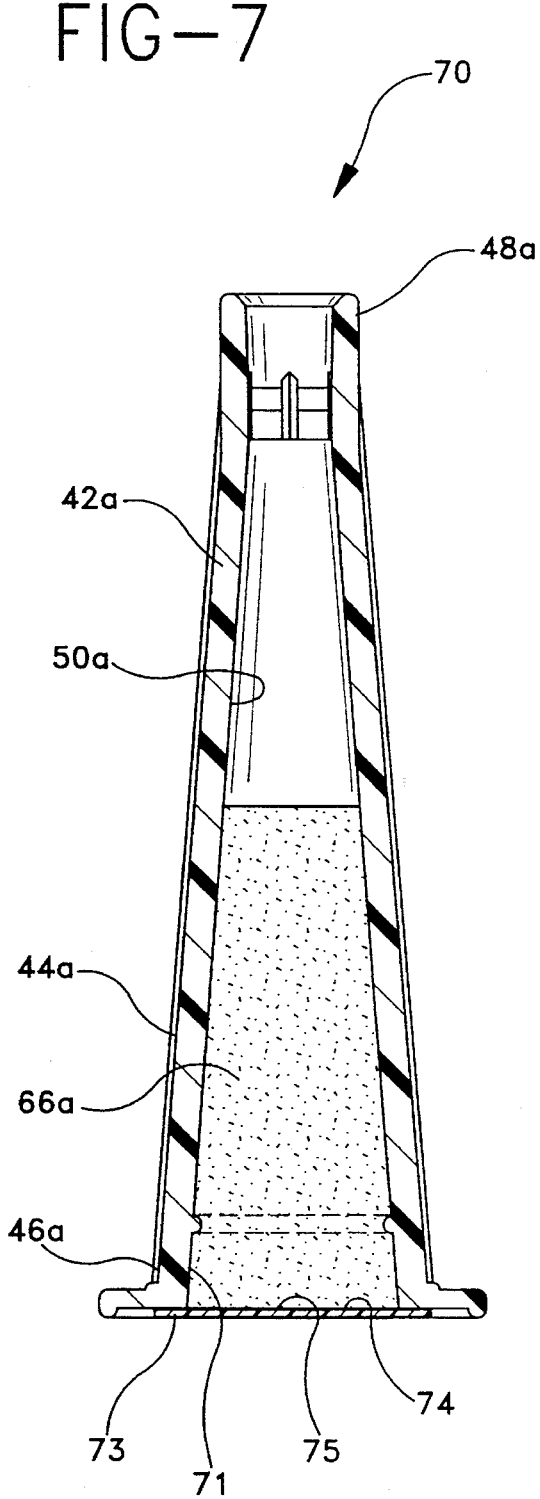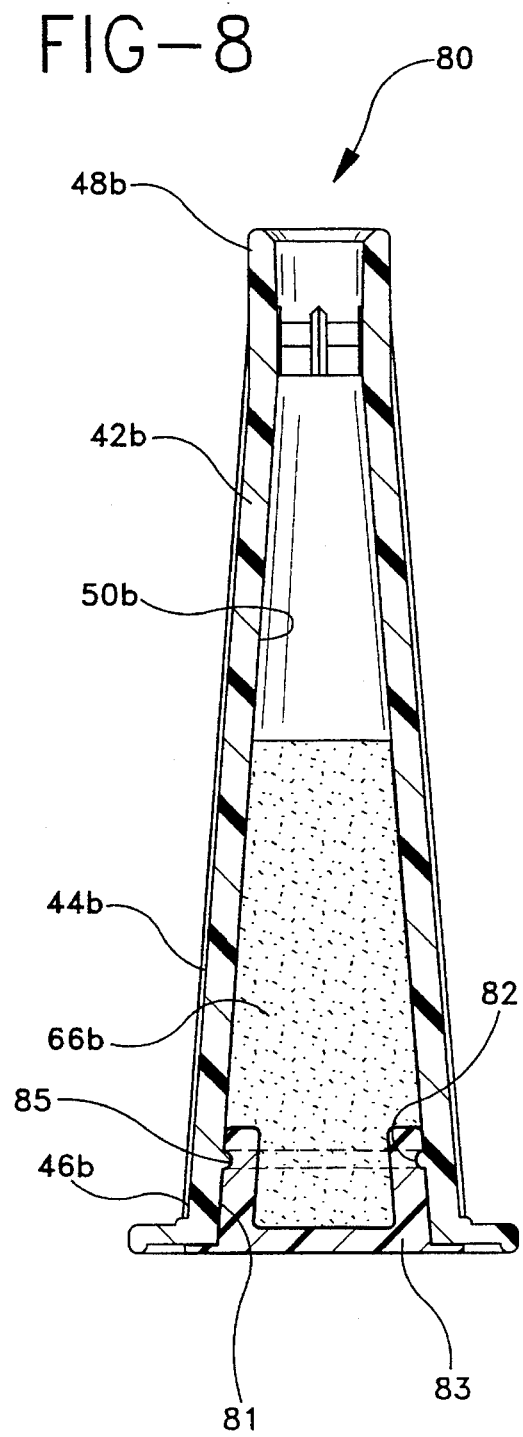

5,483,973

NEEDLE STOPPER AND NEEDLE REMOVAL DEVICE

This is a continuation-in-part of application Ser. No. 969,496, filed on Oct. 30, 1992, now abandoned.

BACKGROUND OF THE INVENTION

1. Field of the Invention

The subject invention relates to a stopper for a needle of a syringe such as an arterial blood gas syringe, and more particularly to a stopper which enables one-handed covering and sealing of the needle, and a subsequent safe separation and containment of the needle from the syringe barrel.

2. Description of the Prior Art

A hypodermic syringe includes a syringe barrel having an open proximal end and an opposed distal end. A cylindrical wall extends between the proximal and distal ends and defines a fluid receiving chamber in the syringe barrel. The distal end of the syringe barrel includes a passage that extends therethrough and communicates with the chamber. The distal end also is configured to receive a needle cannula which communicates with the passage and the chamber. The prior art hypodermic syringe also includes a plunger in sliding fluid tight engagement with the cylindrical wall of the chamber. Sliding movement of the plunger toward the distal end causes fluid in the chamber to be evacuated through the passage and the needle cannula. Conversely, sliding movement of the plunger toward from the proximal end draws fluid through the needle cannula and the passage and into the chamber.

Most hypodermic needles are provided with needle shields or covers to protect the needle from damage and contamination during shipment and transfer to the patient's room as well as to protect health care workers from accidental needle sticks involving clean unused needles. The needle shield or cover typically is removed immediately prior to use of the hypodermic syringe. A hypodermic syringe that is used for an injection typically will be discarded into a special sharps collector immediately after injection to further protect against accidental needle sticks. However, hypodermic syringes such as arterial blood gas syringes that are used to withdraw fluid from a patient cannot be discarded until the fluid has been properly evaluated. To protect against accidental needle sticks at this stage, the needle cannula may be removed or covered with a needle stopper.

Some medical procedures require periodic sampling and evaluation of arterial blood. For example, blood may be evaluated for content of carbon dioxide, oxygen and pH. Arterial blood may also be evaluated for concentration of electrolytes, such as sodium and potassium.

An arterial blood gas syringe is similar to a hypodermic syringe but it also includes an anticoagulant such as liquid or dry heparin in the chamber to prevent blood clotting. Also, an arterial blood gas syringe usually contains means associated with the plunger which allows gas, such as air, to leave the chamber but blocks the exit of liquid such as blood.

The use of an arterial blood gas syringe for arterial blood gas analysis is difficult for several reasons. Arteries often are deeper in the body of the patient, and hence more difficult to locate. Accordingly, the respiratory therapist, technician or phlebotomist must insert the needle fairy deeply, thereby causing considerable discomfort to the patient. After removal of syringe from the patient, the therapist must immediately apply pressure to the punctured artery to prevent bleeding. Proper evaluation of arterial blood gas requires prompt sealing of the arterial blood sample to prevent reaction of the blood with ambient air. However, the realities of the procedure often require the respiratory therapist to use one hand for applying pressure to the puncture wound, thereby leaving only one hand to seal the needle cannula and to handle the blood filled syringe.

The prior art includes arterial blood gas syringe kits with components to seal the needle cannula after withdrawal from the patient. In particular, a prior art kit includes an arterial blood gas syringe and a cube of rubber, plastic or cork approximately 1 $cm^3$. The therapist usually places the cube on a flat surface near the patient. An arterial blood sample then is obtained in the standard manner. After withdrawing the needle cannula from the patient, the therapist applies pressure to the wound with one hand, while using the other hand to urge the tip of the needle cannula into the cube on the work surface near the patient. The cube occludes the needle cannula to prevent blood/air interaction while the respiratory therapist attends to the hemostasis. The therapist then shakes the syringe to mix the blood and the heparin anticoagulant in the syringe barrel. The needle is then removed by using a hemostat or by hand, and the used needle is discarded into an appropriate safety collector for sharp objects. The syringe tip then is covered with a tip cap. The blood filled syringe with tip cap is usually placed in a container including ice and sent to a laboratory for analysis.

The prior art arterial blood gas kit has several disadvantages. For example, the small rubber cube neither guides nor limits the movement of the needle. Thus, the needle can be skewed during insertion by the respiratory therapist or it can bend during insertion to project from a side surface of the small rubber cube. Similarly, the small cube can tilt during insertion thereby enabling the tip of the needle to pass entirely through the cube. In either case, the tip of the needle is exposed and enables ambient air to react with the arterial blood in the syringe. Furthermore, the exposed tip of the needle can lead to accidental needle stick. Means for removing the needle from the syringe barrel may reduce the risk of accidental needle stick, but a separate removal means in the arterial blood gas kit adds to the complexity.

As noted above, the prior art also includes many types of needle shields that can be placed over the needle to prevent accidental puncture. However, these prior art needle shields generally do not occlude the needle tip, and generally are not well suited for the one-handed sealing that is realistically required for arterial blood gas procedures.

SUMMARY OF THE INVENTION

The subject invention is directed to a needle stopper which enables efficient one-handed occlusion of a needle cannula. The stopper is configured to prevent improper insertion or over insertion of the needle cannula, and thereby helps avoid accidental needle sticks. The stopper also is configured to enable safe efficient removal of the needle cannula from the syringe barrel.

The needle stopper of the subject invention includes a substantially rigid shell having an upstanding generally tubular side wall with opposed top and bottom ends and a needle-receiving chamber therebetween. The height of the tubular side wall, as measured between the top and bottom ends, is greater than the length of the needle cannula to be inserted therein. The bottom of the tubular side wall may be dimensioned and configured to define an efficient support for the upstanding side wall. For example, the side wall may be of frustoconical or pyramidal shape, with the bottom end of the side wall defining a greater cross-sectional area than the top end. It is an important advantage of the present invention that the outwardly tapering side wall of the shell minimizes the possibility of the needle tip engaging the side wall before complete insertion of the needle cannula into the shell. Engagement of the side wall by the needle before complete insertion could cause the sharp needle point to pass through the side wall and project outwardly therefrom. The shell may also include a support flange extending outwardly from the bottom end of the side wall to ensure support of the shell in an upright orientation.

The top end of the shell is open and dimensioned to enable insertion of the needle cannula therein. The top end of the shell may further be configured to engage a needle hub and to facilitate the separation of the hub from a syringe barrel.

The needle stopper of the subject invention further includes a sealing material in the needle-receiving chamber. The sealing material is selected to permit easy penetration of the needle cannula, while simultaneously occluding the needle tip to prevent deterioration of the arterial blood sample. For example, the sealing material may comprise clay, wax or certain rubbers and plastics, or other suitable materials.

The subject invention may also be directed to a kit of parts for efficiently and safely drawing and protecting a sample of arterial blood gas. The kit of parts may include an arterial blood gas syringe assembly containing anticoagulant such as heparin, and the above described needle stopper. The kit may further include a tip cap for protectively enclosing the passage through the syringe barrel after removal of the needle hub therefrom.

The needle stopper of the subject invention is usually used by initially supporting the bottom end on a work surface in proximity to the patient. A respiratory therapist then removes the shield from the needle cannula and draws an arterial blood sample. The respiratory therapist uses one hand to withdraw the needle from the patient, and the other hand to apply pressure to the puncture wound. While maintaining pressure with one hand, the respiratory therapist inserts the tip of the needle cannula into the open top end of the needle stopper. The needle cannula is advanced sufficiently for the needle tip to enter the sealing material and for the needle hub to engage the top end of the shell. The therapist then mixes the blood and the anticoagulant, such as heparin, in the syringe barrel. When hemostasis has been achieved, the therapist engages the syringe barrel in one hand and the shell of the needle stopper in the other hand. Movement of the syringe barrel relative to the needle stopper separates the needle hub from the syringe barrel. The passage of the syringe barrel then is capped and the safely connected needle cannula, hub and stopper are discarded in a sharps collector. Finally, the efficiently sealed arterial blood sample is sent to the laboratory for analysis.

BRIEF DESCRIPTION OF THE DRAWINGS

FIG. 2 is a side elevational view of the needle stopper illustrated in FIG. 1;

FIG. 3 is a cross-sectional view taken along line 3—3 in FIG. 2;

FIG. 7 is a cross-sectional view of an alternate embodiment of the needle stopper of the present invention; and FIG. 8 is a cross-sectional view of another alternative embodiment of the needle stopper of the present invention.

DETAILED DESCRIPTION OF THE PREFERRED EMBODIMENTS

Figure 1:
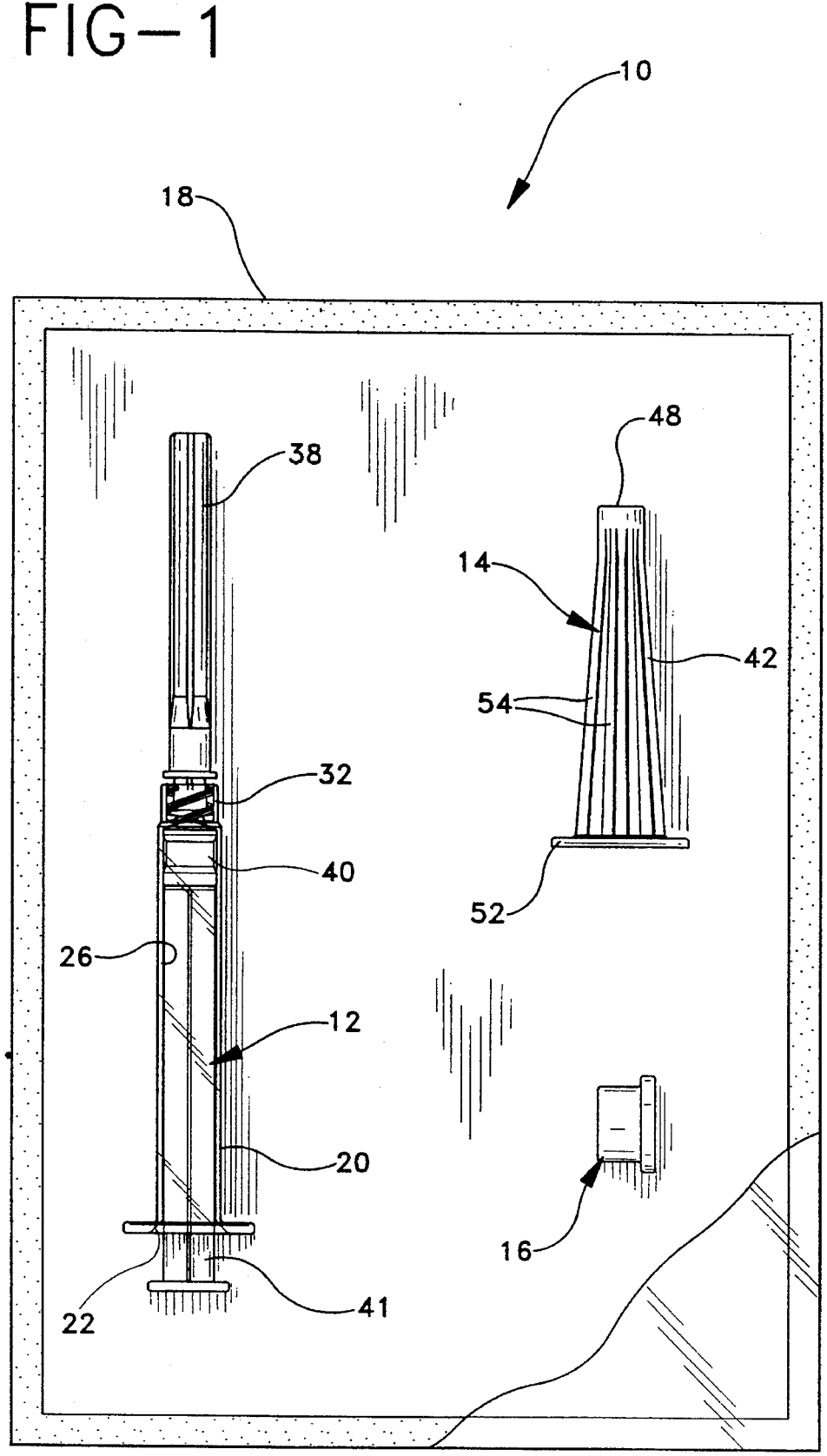
FIG. 1 is a top plan view, partly in section, of a kit of components for drawing a sample of arterial blood.

A kit of components for an arterial blood gas procedure is identified generally by the numeral 10 in FIG. 1. The kit includes a hypodermic syringe 12, a needle stopper 14 and a tip cap 16 all of which are protectively enclosed in a sealed protective package 18 which can be made of many materials and structures including foil and plastic sheet material.

Arterial blood gas syringe 12 includes a generally cylindrical syringe barrel 20 having an open proximal end 22, a distal end 24 and a fluid receiving chamber 26 extending therebetween. The chamber contains an anticoagulant such as liquid or dry heparin. The distal end of syringe barrel 20 includes a tip 28 having a passage 30 extending axially therethrough and communicating with the chamber. A collar 32 is preferably disposed coaxially around syringe tip 30 and is provided with an array of internal threads. A needle cannula 34 is rigidly mounted to a hub 36 which is removably engaged with the internal threads of collar 32 at the distal end of syringe barrel 20. The syringe can also be made without a collar wherein the hub is held onto the barrel through a frictional interference fit between the tip and the hub. A shield 38 is removably engaged over the needle cannula to avoid accidental needle sticks and contamination prior to use.

A sealing plug or stopper assembly 40 is mounted to the distal end of a plunger rod 41 and is in sliding fluid tight engagement with the syringe barrel. The sealing plug of an arterial blood gas syringe may include a filter, such as a hydrophobic filter, to permit air to pass from the blood receiving space in the chamber while preventing the flow of blood beyond the sealing plug. Accordingly, the stopper 40 initially acts as a vent plug and later as a sealing plug when the filter is contacted by blood. Such a stopper is taught in U.S. Pat. No. 4,340,067.

Tip cap 16 of the arterial blood gas kit is dimensioned and configured to engage tip 28 of syringe barrel 20 for sealing passage 30 therethrough and preventing a reaction between ambient air and arterial blood in chamber 26. Tip caps are usually made of rubber and include a closed end cavity that receives a syringe tip. As will be explained further herein, the tip cap may be mounted to syringe tip 28 after needle cannula 34 and hub 36 have been separated. A typical tip cap is illustrated in U.S. Pat. No. 4,444,310.

Figure 4:
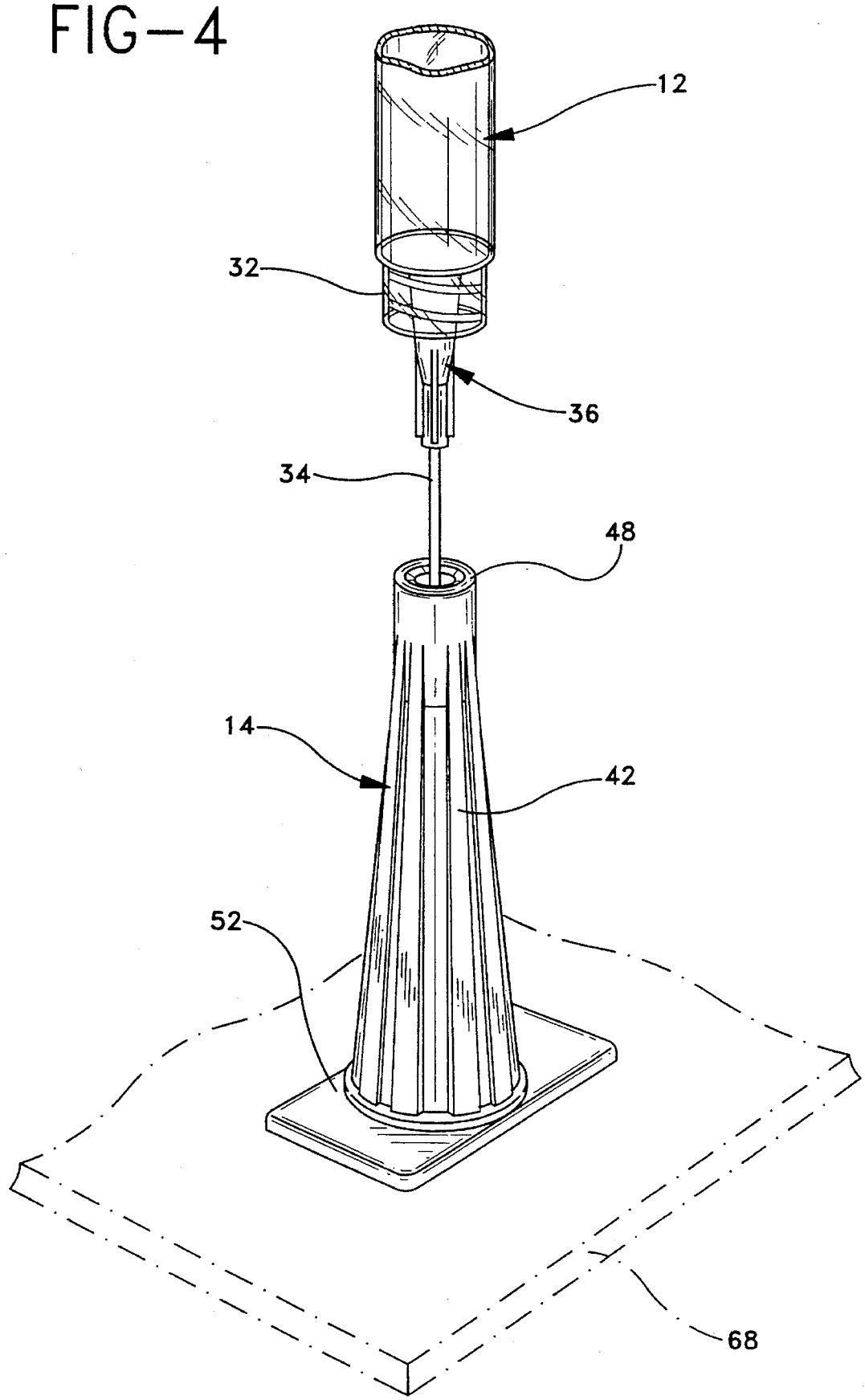
FIG. 4 is an exploded perspective view of an arterial blood gas syringe and a needle stopper in accordance with the subject invention.

Needle stopper 14 is illustrated in greater detail in FIGS. 2, 3 and 4. The stopper includes a shell 42, which preferably is unitarily molded from a thermoplastic material exhibiting rigidity, hardness and resistance to needle puncture. However, the shell may be made of glass, metal or other materials resistant to needle puncture. Shell 42 includes a generally frustoconical side wall 44 having a bottom end 46, an opposed open top end 48 and a needle-receiving chamber 50 defined within the side wall and extending between bottom and top ends 46 and 48. The frustoconical side wall of shell 42 defies a height "A", as depicted in FIG. 2, which exceeds the overall length of that portion of needle 34 which projects out of hub 36 on the arterial blood gas syringe. Frustoconical side wall 44 is configured such that the top end thereof defines the minor cross-sectional dimension and the bottom end thereof defines the major cross-sectional dimension. As will be explained further herein, this configuration is an important advantage of the present invention because it reduces the potential of a needle inserted into open top end 48 from snagging or piercing side wall 44 as the needle is advanced into chamber 50. The orientation of frustoconical side wall 44 also contributes to stability of needle stopper 14. Stability is further enhanced by a generally planar base 52 extending outwardly from bottom end 46 and defining a major cross-sectional dimension for shell 42.

The frustoconical side wall of shell 42 is characterized by a plurality of longitudinally extending ribs 54 extending outwardly therefrom. The ribs define surface irregularities that facilitate gasping and rotation of the needle stopper as explained further herein.

Open top end 48 of frustoconical side wall 44 is preferably characterized by an outwardly directed needle entry chamber 56 leading into the needle-receiving chamber. It is also within the purview of this invention to provide a flared structure at the open top end to help guide the needle into the needle-receiving chamber. A hub-engaging section 58 of needle-receiving chamber 50 is disposed directly below chamfer 56 and is tapered slightly inwardly to conform to the shape of the needle hub on the arterial blood gas syringe.

The frustoconical side wall of shell 42 is further characterized by a plurality of inwardly directed locking protrusions 64 in proximity to open top end 48. The locking protrusions are dimensioned to engage the outer surface regions of the needle hub after sufficient insertion of the needle cannula into needle-receiving chamber 50.

The needle stopper is further characterized by a sealing material 66 disposed in needle-receiving chamber 50 of shell 42 from a location adjacent the bottom to a location intermediate the top and bottom. The sealing medium may be made of clay, wax, natural rubber, synthetic rubber, thermoplastics, thermoplastic elastomers or polymeric foam that will not prevent penetration of the needle cannula, and that will occlude or prevent environmental air contact to the interior of the needle tip after sufficient insertion into needle-receiving chamber 50.

Arterial blood gas kit 10, as shown in FIG. 1 is used by initially opening the package 18 and extracting syringe 12 and needle stopper 14. Base 52 of shell 42 of the needle stopper is positioned on a work surface of a variety of orientations, with horizontal surface 68 being preferred, in proximity to the patient, as shown in FIG. 4, such that top end 48 of frustoconical side wall 44 projects upwardly from horizontal surface 68. The respiratory therapist will then remove needle shield 38 from syringe barrel 20 to expose needle cannula 34. The therapist will then insert the tip of needle cannula 34 into a selected artery of the patient and will cause blood to be drawn into chamber 26 of the syringe barrel. After a sufficient quantity of arterial blood has been drawn into syringe barrel 26, the therapist will exert forces on the syringe barrel with one hand to withdraw needle cannula 34 from the patient. The therapist will then immediately use his or her other hand to apply pressure to the puncture wound for achieving hemostasis.

Figure 5:
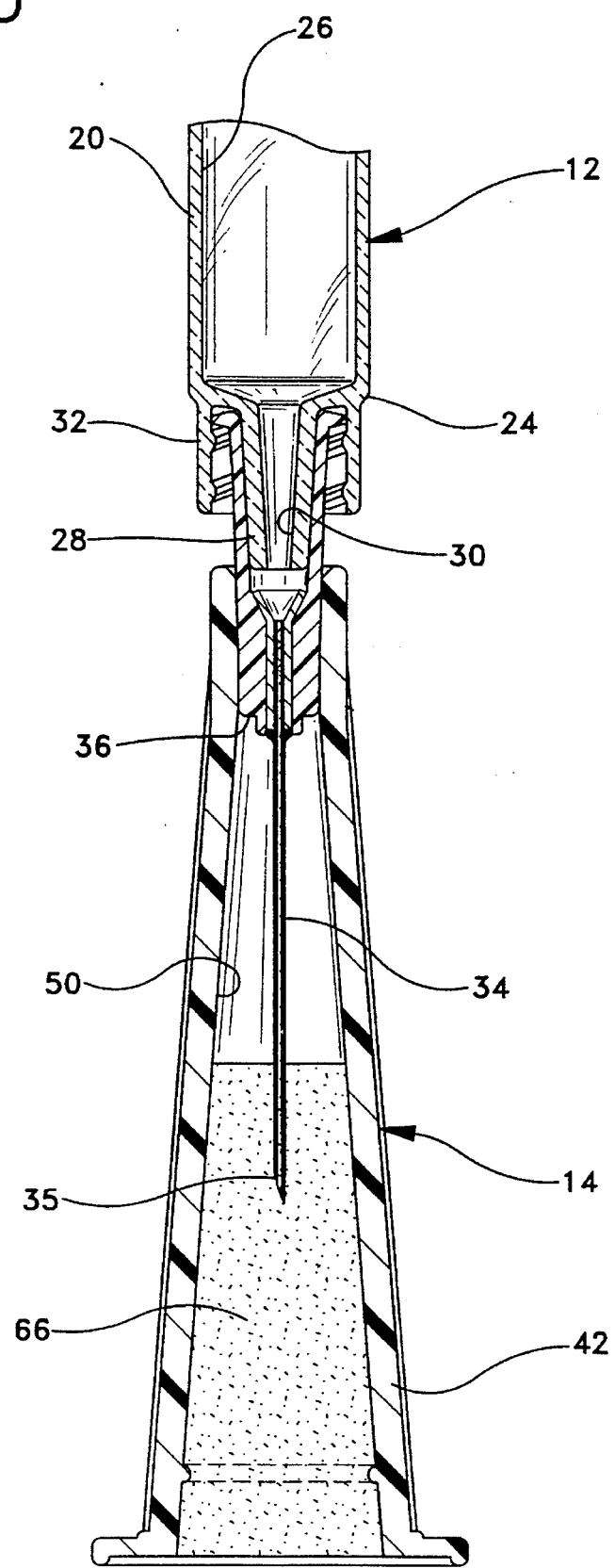
FIG. 5 is a cross-sectional view similar to FIG. 3, but showing the needle of the arterial blood gas syringe sealingly disposed in the needle stopper.
Figure 6:
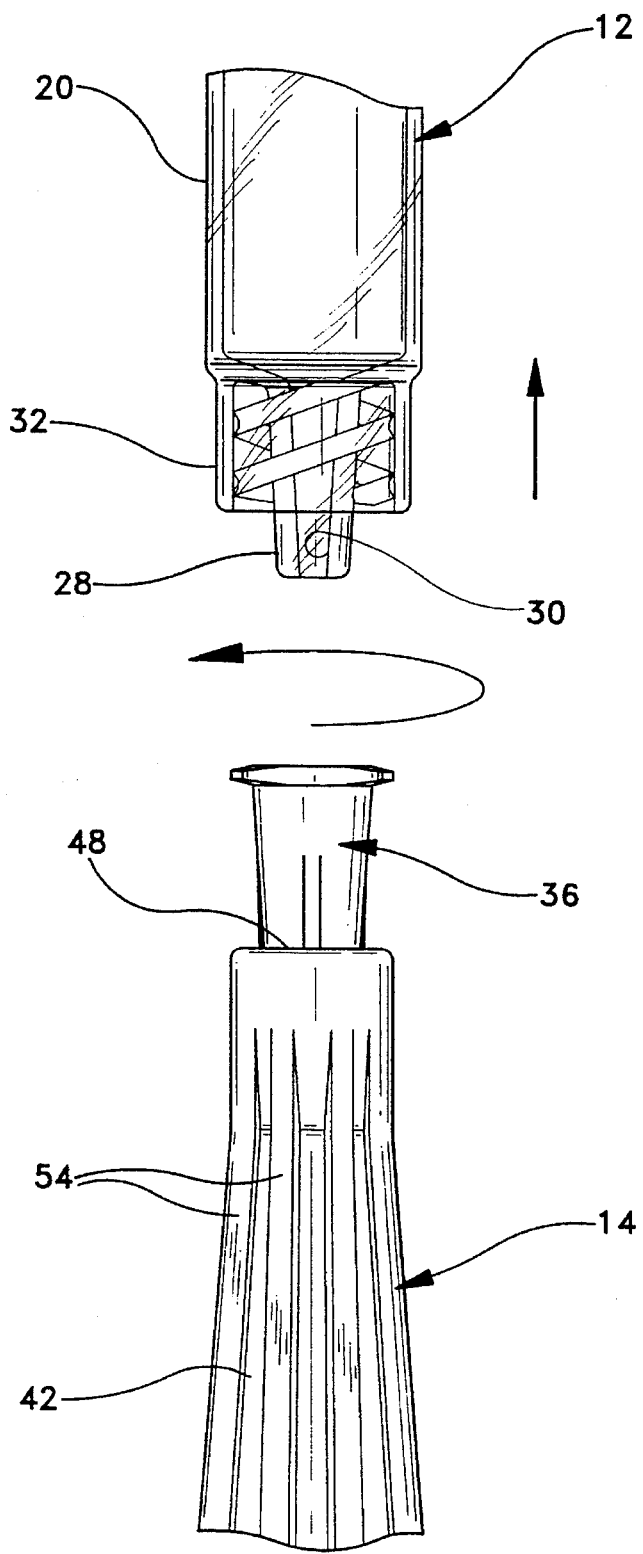
FIG. 6 is a side elevational view of the needle cannula and hub engaged in the needle stopper and separated from the syringe.

As noted above, it is necessary to seal tip 38 of needle cannula 34 quickly to prevent reaction between the arterial blood and ambient air. It also is important to protect the patient and health care workers from accidental needle sticks. The therapist achieves both objectives by aligning the syringe with the longitudinal axis of needle stopper 14, and placing the tip of needle cannula 34 into open end 48 of shell 42. The respiratory therapist then advances needle cannula 34 into open top end 48 as shown in FIG. 4. After sufficient advancement, tip 35 of needle cannula 34 will be sealingly engaged by the sealing material 66. A therapist will continue the axial advancement of the syringe until needle hub 36 is engaged by locking protrusions 64 adjacent open top end 48 of the shell of needle stopper 14 as shown in FIG. 5. It should be emphasized that this insertion of needle cannula 34 into the needle-receiving cavity of shall 42 can be achieved by one hand while the respiratory therapist continues to apply pressure to the puncture wound of the patient. After complete seating of needle cannula 34 and needle hub 36 in needle-receiving cavity 50, the therapist may move the syringe, such as by rotation and/or inversion, to mix heparin preloaded in the syringe chamber with the arterial blood.

Once hemostasis has been achieved, the therapist may remove the pressure from the puncture wound. The therapist may then grasp the arterial blood gas syringe with one hand and the needle stopper with the other hand. Axial movement of needle stopper 14 toward syringe 12 will assure the therapist of complete seating of stopper 14 onto needle hub 36. The therapist may then rotate needle stopper 14 relative to syringe barrel 20. Locking protrusions 64 on the shell of needle stopper 14 cause the needle hub to rotate with the needle stopper and to disengage from threaded collar 32 and syringe tip 28 at the distal end of syringe barrel 20. This removal step may also be accomplished in a one-handed procedure if hemostasis has not yet occurred. The separated needle cannula 34, needle hub 36 and needle stopper 14 may be discarded immediately into an appropriate sharps container. It is an advantage of this invention that, because the tip of the needle is sealed by the sealing material, blood in the needle is not likely to come out of the unsealed end of the needle during the disposal step. Tip cap 16 may then be engaged over the tip of syringe barrel 12 to seal the syringe and reduce the probability of reaction between the arterial blood gas and ambient air. The sealed arterial blood gas syringe may then be placed in a plastic bag containing ice transported directly to the laboratory for analysis of blood gas content.

Referring to FIG. 7, an alternative embodiment of the present needle stopper is illustrated. In this alternative embodiment, the structure of the needle stopper is substantially identical to the needle stopper of FIGS. 1–6. Accordingly, components that are substantially identical to components of FIGS. 1–6 are numbered identically to the components of the embodiments of FIGS. 1–6, except a suffix "a" will be used to identify the elements in FIG. 7. Needle stopper 70 includes a shell 42a having an open top 48a, a bottom 46a having an aperture 71 therein. Penetrable sealing material 66a, such as commonly available modeling clay, is provided. Sealing means is provided to form a barrier between the chamber an the environment at bottom end 46a. In this embodiment the sealing means includes elements 73 having a top surface 74 having an adhesive coating 75. In this embodiment, the element 73 is an adhesive coated laminate of paper and plastic which is preferably made of material having the same color as the shell so that the needle shield appears to be one piece or unitary when viewed from the bottom end. Also, when a soft material such as modeling clay is used as the sealing material, element 73 helps keep the material within the shell and also prevents transfer of material out of the shell through inadvertent contact. In manufacture, the element may be applied first if a viscous or setting sealing material is introduced into the shell through open end 48a. If the penetrable sealing material is inserted into the needle shield, during production, from bottom end 46a, element 73 can be attached after the sealing material is in place.

FIG. 8 illustrates another embodiment of the present needle stopper. In this alternative embodiment the structure of the needle stopper is substantially similar to the needle stopper of FIGS. 1–6. Accordingly, substantially similar components that perform substantially similar functions will be numbered identically to those components of the embodiments of FIGS. 1–6 except a suffix "b" will be used to identify the components of FIG. 8.

Alternative needle stopper 80 includes a shell 42b having a bottom 46b and an open top end 48b and a side wall 44b therebetween defining a needle receiving chamber 50b. A penetrable material 66b is disposed in needle-receiving chamber 50b. Bottom 46b of the shell includes aperture 81 and radially inwardly facing circumferential fib 82. The aperture 81 is sealed from the environment, at the bottom of the shell, by a rigid element in the form of cup-shaped plug 83 made of thermoplastic material. Plug 83 includes circumferential annular recess 85 which is shaped to receive and engage fib 82 of the shell so that the plug and the shell engage each other in a snap-fit arrangement designed to lock the plug in place once it is installed. The rigid plug provides a substantial barrier preventing improper insertion of the needle cannula into the bottom end of the needle shield and also for retaining the penetrable sealing material within the shell.

The shell of the needle stopper of the present invention can be made of a wide variety of rigid materials such as thermoplastic, thermosetting plastic, metal, glass, and reinforced plastic material such as fiber reinforced plastic material. Fiberglass reinforced thermoplastic material is preferred because of its low cost and its ability to be molded into a structure which is highly resistant to penetration of the needle cannula. When properly molded it provides a hard, smooth outside surface which makes it difficult to penetrate by a needle cannula even if such attempt is made intentionally. Accordingly, the reinforced thermoplastic material offers the moldability of the thermoplastic and the surface properties approaching glass or metal with respect to needle penetration resistance.

In summary, a needle stopper is provided for one-handed protection and sealing of the needle cannula of an arterial blood gas syringe. The needle stopper includes a rigid shell having a bottom end, an open top end and a needle-receiving chamber therebetween. The bottom end of the shell is configured to support the shell in an upright condition on a generally horizontal surface. A sealing material, such as clay including widely available modeling clay, wax or certain plastics or rubbers is disposed in the needle-receiving chamber to occlude the tip of a needle cannula inserted therein. Occlusion of the needle cannula can be carried out safely with one hand while the respiratory therapist is using the other hand to apply pressure to the puncture wound. After hemostasis has been achieved, the respiratory therapist can use both hands to rotate the needle stopper relative to the syringe barrel. The engagement of the needle stopper with the needle hub will cause the needle hub and the needle cannula attached thereto to threadedly separate from the syringe barrel for safe discard. This removal step can also be done in a one-handed procedure if hemostasis has not yet occurred. The tip of the syringe barrel then can be sealed, and the arterial blood sample can be transported to a laboratory for analysis.

What is claimed is:

1. A method for obtaining a blood sample from an artery using syringe having a syringe barrel with a distal end, a needle hub removably mounted to said distal end, and a needle cannula mounted to said needle hub, said method comprising the steps of:

providing a needle stopper having a shell with a bottom end, an open top end and a side wall defining a needle-receiving chamber therebetween, hub engaging means on said shell for engaging said hub when said needle cannula is inserted into said needle-receiving chamber, said side wall of said needle stopper being tapered such that said needle-receiving chamber defines larger cross-sectional areas at locations thereon closer to said bottom end than said top end, whereby said taper helps prevent engagement of said needle cannula with said side wall during insertion into said needle-receiving chamber, a penetrable sealing material disposed in said needle-receiving chamber;

supporting the bottom end of said shell on a generally horizontal surface;

drawing a sample of blood from said artery with said syringe barrel and said needle cannula;

withdrawing said needle cannula from said artery;

applying pressure to said artery for achieving hemostasis; and inserting said needle cannula of said syringe through said open top end of said shell and into said needle-receiving chamber sufficiently for said needle cannula to be occluded by said sealing material; and moving said shell relative to said syringe barrel for disengaging said needle hub from said syringe barrel.

2. The method of claim 1 further comprising the step of sealing said syringe barrel after removal of said needle hub therefrom.

3. The method of claim 2 further comprising the step discarding said needle stopper with said hub and said needle cannula engaged therein.

\* \* \* \* \*